(12) United States Patent
Campbell et al.

(10) Patent No.: US 10,618,023 B2
(45) Date of Patent: Apr. 14, 2020

(54) FORMATION OF A JANUS MICROCAPSULE

(71) Applicant: International Business Machines Corporation, Armonk, NY (US)

(72) Inventors: Eric Campbell, Rochester, MN (US); Jason Wertz, Pleasant Valley, NY (US); Brandon Kobilka, Tucson, AZ (US); Sarah Czaplewski, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 90 days.

(21) Appl. No.: 15/786,684

(22) Filed: Oct. 18, 2017

(65) Prior Publication Data

US 2019/0111403 A1    Apr. 18, 2019

(51) Int. Cl.
*B01J 13/02* (2006.01)
*B01J 13/04* (2006.01)
*B01J 13/20* (2006.01)
*A61K 9/50* (2006.01)

(52) U.S. Cl.
CPC ............. *B01J 13/04* (2013.01); *A61K 9/5063* (2013.01); *B01J 13/025* (2013.01); *B01J 13/20* (2013.01); *A61K 9/5015* (2013.01); *A61K 9/5021* (2013.01)

(58) Field of Classification Search
CPC .......... B01J 13/04; B01J 13/025; B01J 13/20; A61K 9/5015; A61K 9/5021; A61K 9/5063
See application file for complete search history.

(56) References Cited

U.S. PATENT DOCUMENTS

| | | | |
|---|---|---|---|
| 8,349,309 B2 | 1/2013 | Santerre et al. | |
| 2007/0231355 A1* | 10/2007 | Quadir | A61K 8/0245 424/401 |
| 2010/0239659 A1 | 9/2010 | Diwan et al. | |
| 2014/0120162 A1 | 5/2014 | Mathiowitz et al. | |
| 2017/0119891 A1 | 5/2017 | Lal et al. | |

OTHER PUBLICATIONS

Perro et al, "Design and synthesis of Janus micro- and nanoparticles" J. of Mat. Chem., 2005, 15, 3745-60.*
Li et al., "Layer-by-Layer Assembed Janus microcapsules" Macromolecules, 2005, 38, 7876-79.*
Gu, et al., "Narrow Sized Dual-functional Microcapsules: Contact Infection Control and Drug Delivery," Manitoba Health Research Council (MHRC) Operating and Establishment Grants, printed May 31, 2017, 29 pages.
Han, et al., "Synthesis of fluorinated monomer and formation of hydrophobic surface therefrom," RSC Advances, Royal Society of Chemistry, RSC Adv., 2015, 5, 22847, 9 pages.
Indalkar, et al., "Janus Particles Recent and Novel Approach in Drug Delivery: An Overview," Current Pharma Research, Accepted Aug. 17, 2013, Available Online Sep. 14, 2013, 3 (4), 2013, pp. 1031-1037.
Stanciu, et al., "Magnetic Particle-Based Hybrid Platforms for Bioanalytical Sensors," ip.com, PubMed Central Id: 3348820, DOI: 10.3390/s90402976, Published Apr. 23, 2009, 23 pages.
You, et al., "Bioresponsive matrices in drug delivery," ip.com, PubMed Central Id: 3002303, DOI: 10.1186/1754-1611-4-15, Published Nov. 29, 2010, 13 pages.
Wikipedia, "Self-healing Material," Printed Oct. 10, 2017, 14 pages, https://en.wikipedia.org/wiki/Self-healing_material.
Blaiszik et al., "Self-Healing Polymers and Composites," Annual Reviews, DOI: 10.1146/annurev-matsci-070909-104532, First published online as a Review in Advance on Apr. 5, 2010, Copyright 2010 by Annual Reviews, 35 pages, http://sottosgroup.beckman.illinois.edu/nrs098.pdf.
Blaiszik et al., "Self-Healing Polymers and Composites," Annual Reviews, Supplemental Material, DOI: 10.1146/annurev-matsci-070909-104532, 2010, 4 pages, http://www.annualreviews.org/article/suppl/10.1146/annurev-matsci-070909-104532?file=mr-40-blaiszik.pdf&.
Wikipedia, "Micro-encapsulation," Printed Oct. 10, 2017, 4 pages, https://en.wikipedia.org/wiki/Micro-encapsulation.
Singh et al., "Microencapsulation: A promising technique for controlled drug delivery," National Institute of Health, Research in Pharmaceutical Sciences, Jul.-Dec. 2010; 5(2): 65-77, 10 pages https://www.ncbi.nlm.nih.gov/pmc/articles/PMC3093624/.

* cited by examiner

*Primary Examiner* — Irina S Zemel
(74) *Attorney, Agent, or Firm* — Peter Edwards (57) ABSTRACT

Microcapsules with a plurality of functionalities on the surface, an article of manufacture including microcapsules with a plurality of functionalities on the surface, and a method of forming a microcapsule with a plurality of functionalities on the surface which includes: providing one or more microcapsules; forming one or more wax particles, the wax particles including a wax core with the one or more microcapsules partially embedded in the wax core; functionalizing a first exposed surface of the one or more microcapsules; removing the functionalized one or more microcapsules from the wax core; and functionalizing a second exposed surface of the functionalized one or more microcapsules, the second exposed surface previously embedded in the wax core are disclosed.

12 Claims, 6 Drawing Sheets

FORMATION OF A JANUS MICROCAPSULE

BACKGROUND

The present disclosure relates to microcapsules and, more specifically, microcapsules with a plurality of functionalities on the surface.

Microcapsules are small capsules with a payload core in the center and a shell surrounding the payload. Payloads may be self-healing agents, disinfectants, repellants (e.g., fluid, insect, or any type of repellant), or any other substances. Microcapsules have applications in a wide variety of fields such as medicine, food, feed, electronics, graphics and printing, photography, textile, waste treatment, agriculture, chemical industry, pharmaceuticals, biotechnology, household and personal care, veterinary, etc.

SUMMARY

Various embodiments are directed toward microcapsules with a plurality of functionalities on the surface. Additional embodiments are directed to an article of manufacture including microcapsules with a plurality of functionalities on the surface. Additional embodiments are directed to a method of forming a microcapsule with a plurality of functionalities on the surface. The method may include providing one or more microcapsules. The method may further include forming one or more wax particles, the wax particles including a wax core with the one or more microcapsules partially embedded in the wax core. The method may further include functionalizing a first exposed surface of the one or more microcapsules. The method may further include removing the functionalized one or more microcapsules from the wax core. The method may further include functionalizing a second exposed surface of the functionalized one or more microcapsules, the second exposed surface previously embedded in the wax core.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to microcapsules and, more specifically, microcapsules with a plurality of functionalities on the surface. While the present disclosure is not necessarily limited to such applications, various aspects of the disclosure may be appreciated through a discussion of various examples using this context.

Microcapsules are widely used as release systems containing payloads within their cores. In various embodiments, microcapsules, as referred to herein, may include nanocapsules. The rupture and eventual release of the payload may be dependent on breaking, or rupturing, a polymer shell of the microcapsule, which may be done through scratching; puncturing; dissolving; disintegrating; using polymers with known or tunable rates of degradation; applying radiation; biological, chemical, photo, thermal, electrical, and magnetic stimuli; or other mechanical or chemical means applied to the polymer surface. In some embodiments, it may be useful to functionalize, or add functional groups (i.e., moieties that contribute to a compound's reactivity), to bind to various molecules or materials. Each functional group may have the capability to bind with different materials or substances, which may improve the range of capabilities of a single microcapsule.

The present disclosure provides a microcapsule with multiple (e.g., two or more) functionalities on the microcapsule surface, herein referred to as a Janus microcapsule. These functionalities may be on different sides of the microcapsule surface. The Janus microcapsule may also carry a payload in its core. In some embodiments, multiple functionalities may be multiple functional groups. Each of the functionalities may be concentrated on different areas of a microcapsule shell. In some embodiments, there is some overlap between the different functionalities. In an embodiment, when a Janus microcapsule has two functionalities, one functionality may be on one half of the Janus microcapsule shell and one functionality may be on the other half of the Janus microcapsule shell. For example, the Janus microcapsule may find use related to drug delivery, with bound magnetic particles on one half of the microcapsule shell and a biomolecule-bonding functionality on the other half of the microcapsule shell. Here, the payload may be a drug that is to be delivered. In another example, the Janus microcapsule may be used in surface abrasion recovery and limitation, with a matrix bonding functionality on one side and a fluorinated moiety on the opposite side. Here, the payload agent may be a self-healing agent. In various embodiments, binding may be a weaker form of bonding, therefore bonding, as discussed herein, may also include binding.

Figure 1:
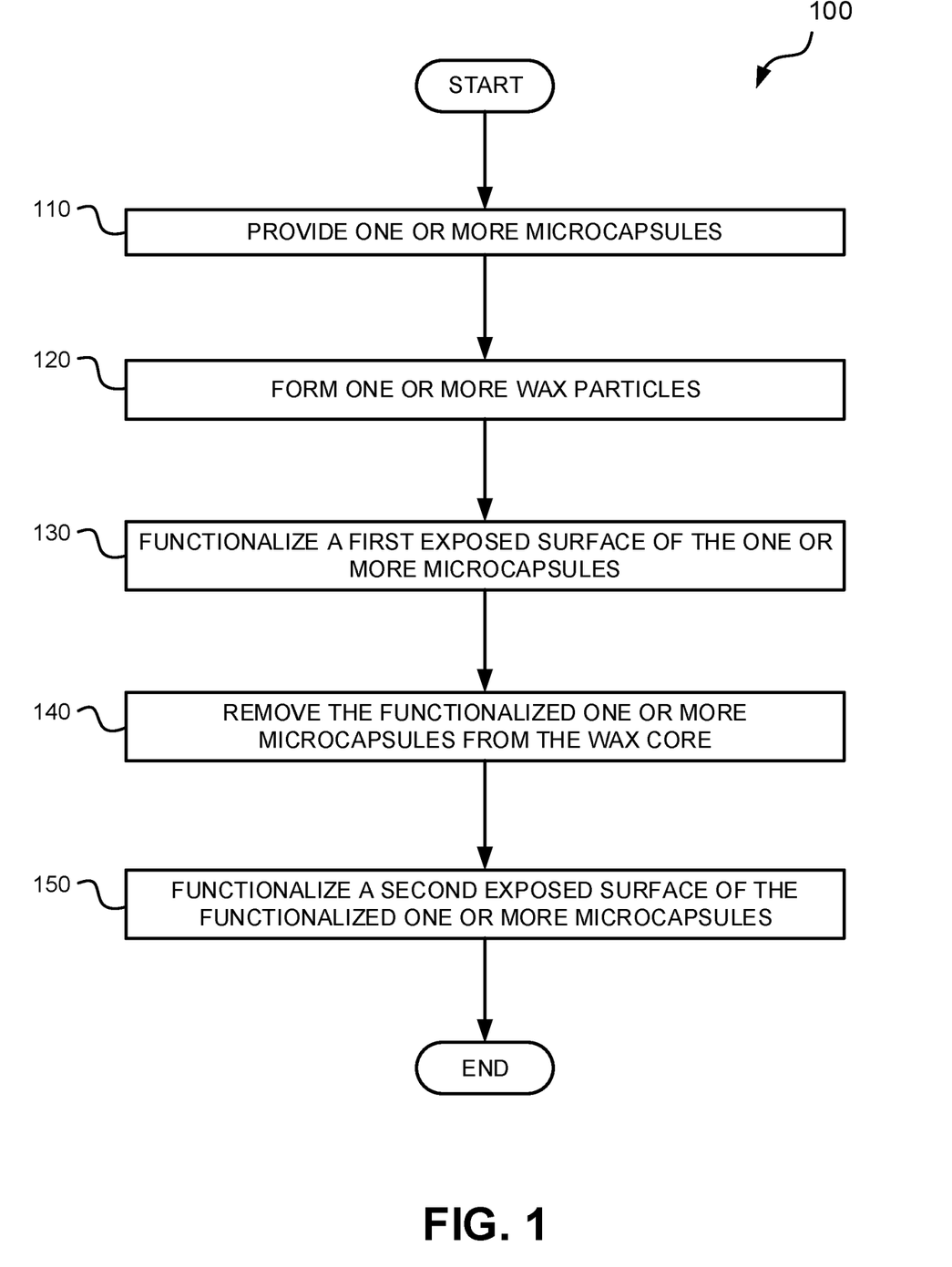
FIG. 1 depicts a flowchart of a set of operations for forming a Janus microcapsule, according to various embodiments.
Figure 5:
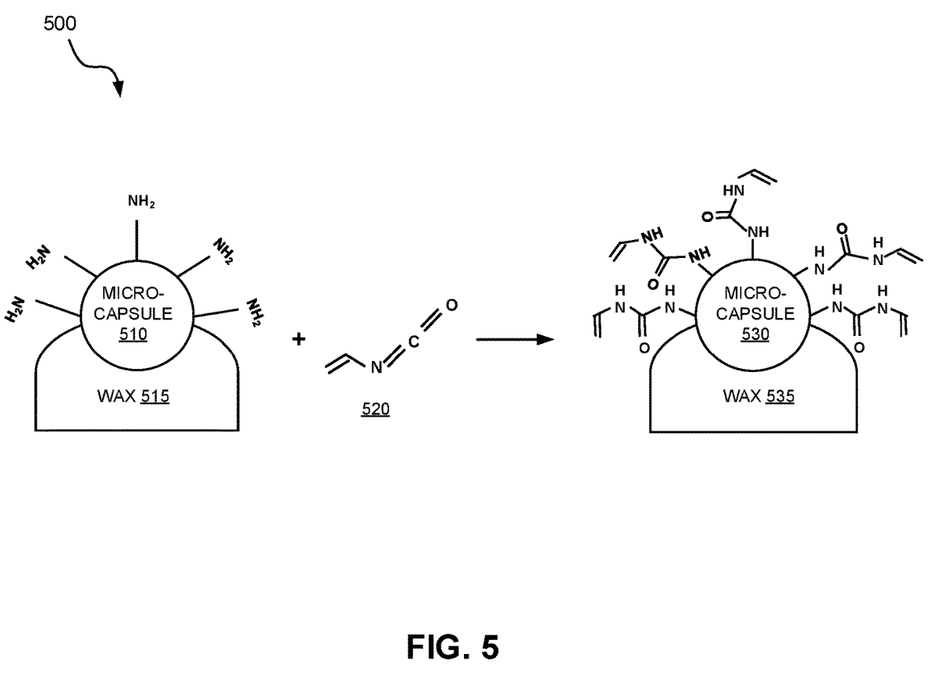
FIG. 5 depicts a chemical reaction diagram illustrating a process of functionalizing a surface of a microcapsule, according to various embodiments.

Referring now to FIG. 1, a flowchart 100 of a set of operations for forming a Janus microcapsule is depicted, according to various embodiments. The Janus microcapsule may be a microcapsule with multiple functionalities (e.g., two or more) on a surface, or shell, of the microcapsule. In some embodiments, a functionality may be a functional group (i.e., moieties that contribute to a compound's properties and reactivity). In an example embodiment, the Janus microcapsule is Janus microcapsule 510 (FIG. 5).

Figure 4:
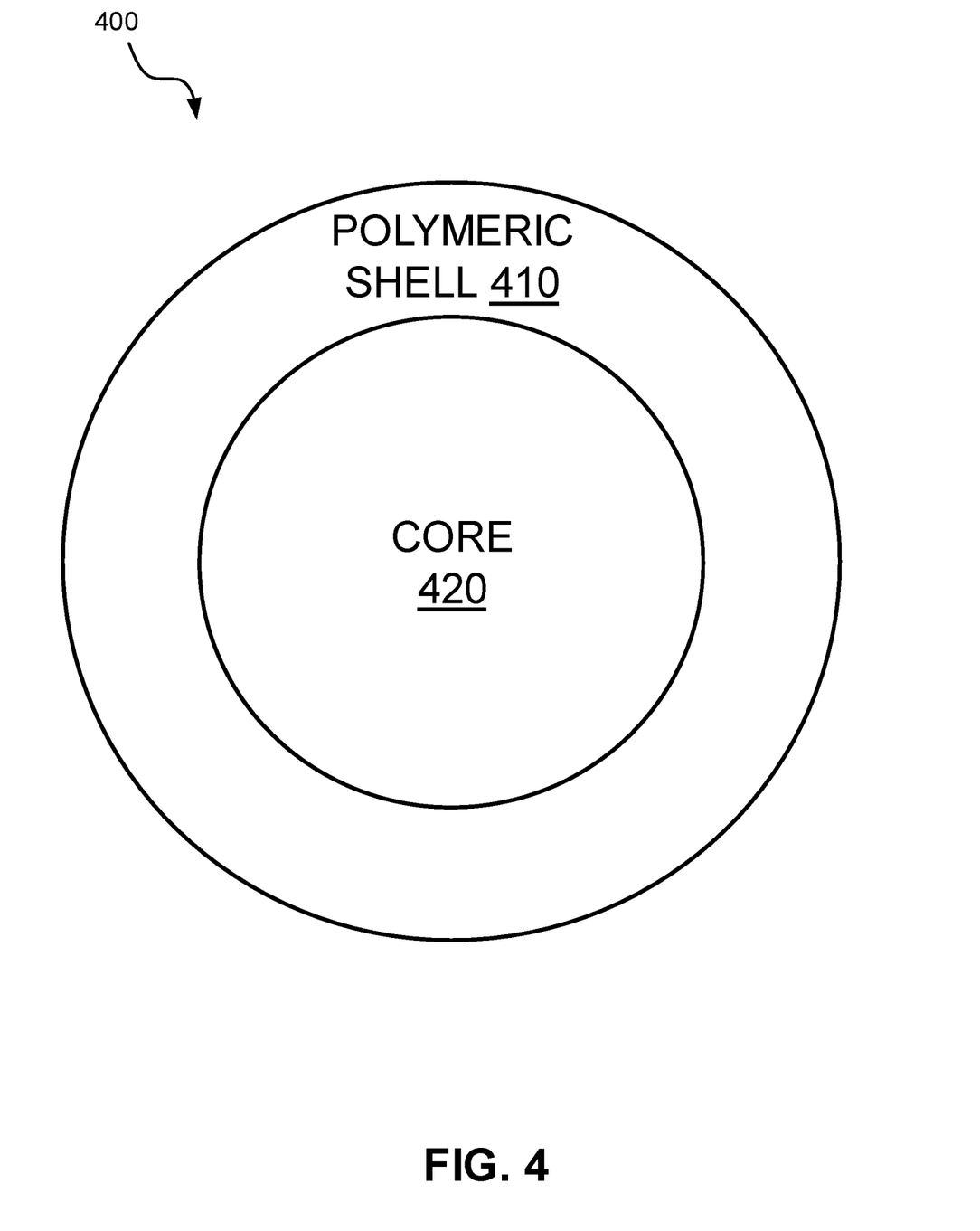
FIG. 4 depicts a schematic diagram of a microcapsule, according to various embodiments.

In various embodiments, process 100 begins with operation 110 to provide one or more microcapsules. In some embodiments, the one or more microcapsules may be microcapsule 400 (FIG. 4). In various embodiments, the one or more microcapsules may have a self-healing payload in the core. Examples of self-healing payloads may include dicyclopentadiene, benzylidene-bis(tricyclohexylphosphine)dichlororuthenium, ethylidene norbornene (ENB), epoxy resin, solid epoxy, Linseed oil, hydroxy end-functionalized poly(dimethyl siloxane) (HOPDMS) and poly(diethoxy siloxane) (PDES) compounds, and other self-healing payloads. The one or more microcapsules may be pre-formed using known methods, in various embodiments. In other embodiments, providing the one or more microcapsules may include forming the one or more microcapsules. The microcapsules may be formed using methods such as emulsion (e.g., oil in water emulsion), matrix polymerization, interfacial polycondensation, interfacial cross-linking, in situ polymerization, coacervation phase separation, complex emulsion, meltable dispersion, powder bed methods, air suspension, pan coating, spray drying, centrifugal extrusion, vibrational nozzle, etc.

An example process for forming a microcapsule with a self-healing dicyclopentadiene core may include mixing deionized water with an ethyl methyl acrylate (EMA) copolymer solution (e.g., 5.0 wt % EMA) to form an aqueous solution. The aqueous solution may then be suspended in a temperature-controlled water bath. Urea, ammonium chloride, and resorcinol may then be added to, and dissolved in, the aqueous solution. Sodium hydroxide and concentrated hydrochloric acid (e.g., 10 wt %) may be added to increase the pH of the reaction. To eliminate surface bubbles, 1-octanol may be added. A slow stream of dicyclopentadiene may then be added to form an emulsion, and then may be allowed to stabilize for a period of time (e.g., 10 minutes). After stabilization, a formaldehyde solution (e.g., 37 wt %) may be added to the emulsion. The emulsion may then be covered, heated, and mixed. After a period of time (e.g., 4 hours) of continuous agitation, the emulsion may be allowed to cool to ambient temperature. After cooling, the emulsion may be separated in vacuo (e.g., in a vacuum) with a filter (e.g., a coarse-fritted filter). The microcapsule is then formed, and may be rinsed with deionized water and then dried for a period of time. It should be noted that a modified resorcinol may be used in place of standard resorcinol, to allow for orthogonal functionality and to increase the hydrophilicity closer to the hydrophilicity of a silica particle. This process is only one possible process of forming a microcapsule, and is discussed for example purposes.

In various embodiments, process 100 continues with operation 120 to form one or more wax particles. The wax particles may include a wax core with the one or more microcapsules partially embedded in the wax core. In some embodiments, the wax particle may be wax particle 335 (FIG. 3). Forming the wax particles is further discussed herein and depicted in FIG. 2.

In various embodiments, process 100 continues with operation 130 to functionalize a first exposed surface of the one or more microcapsules. Functionalizing the exposed surface yields a partially functionalized microcapsule, where a partially functionalized microcapsule is a microcapsule with a functionalized portion (e.g., half) of its surface. In various embodiments, the exposed surface of the microcapsule is half of the microcapsule surface. In some embodiments, functionalizing a particle includes adding functional groups to the particle. Functionalizing the exposed surface of the one or more microcapsules may include introducing a first functionality to the microcapsule. In some embodiments, introducing a first functionality may include reacting a molecule containing the functionality, or functional group, with the exposed microcapsule surface. Example functionalities, or functional groups, include alkanes, alkenes, alkynes, phenyls, amines, alcohols, ethers, esters, thiols, aldehydes, ketones, carboxylic acids, amides, etc. In certain embodiments, the first functionality may be a matrix bonding functionality (e.g., vinyls, amines, epoxies, allyls, acrylates, etc.).

In some embodiments, the provided one or more microcapsules are already functionalized (e.g., the shell of the microcapsule includes a functional group). In these embodiments, functionalizing a first exposed surface of the one or more microcapsules may include adding a functional group to, or reacting a functional group with, the exposed surface of the microcapsule, where the exposed surface of the microcapsule includes a functional group. Reaction 500 (FIG. 5) is one possible reaction for functionalizing the exposed surface of the microcapsule when the shell of the microcapsule includes an existing functional group.

In various embodiments, process 100 continues with operation 140 to remove the functionalized one or more microcapsules from the wax core. After the functionalization synthesis step (operation 130), the microcapsules may be removed from their wax confines (the wax core) to yield the Janus type microcapsules. In some embodiments, a hydrocarbon solvent is used to dissolve the wax, freeing the microcapsule from the wax core. Examples of hydrocarbon solvents may include benzene, hexane, heptane, kerosene, pentane, petroleum, toluene, xylene, or any other hydrocarbon solvents known to dissolve wax. Once the microcapsules are separated from the wax, the microcapsule(s) may be repeatedly washed and separated until no wax remains on the microcapsule. The resulting microcapsule may be a functionalized microcapsule with a portion of the surface functionalized, and a second portion of the surface exposed, but not yet functionalized.

Figure 6:
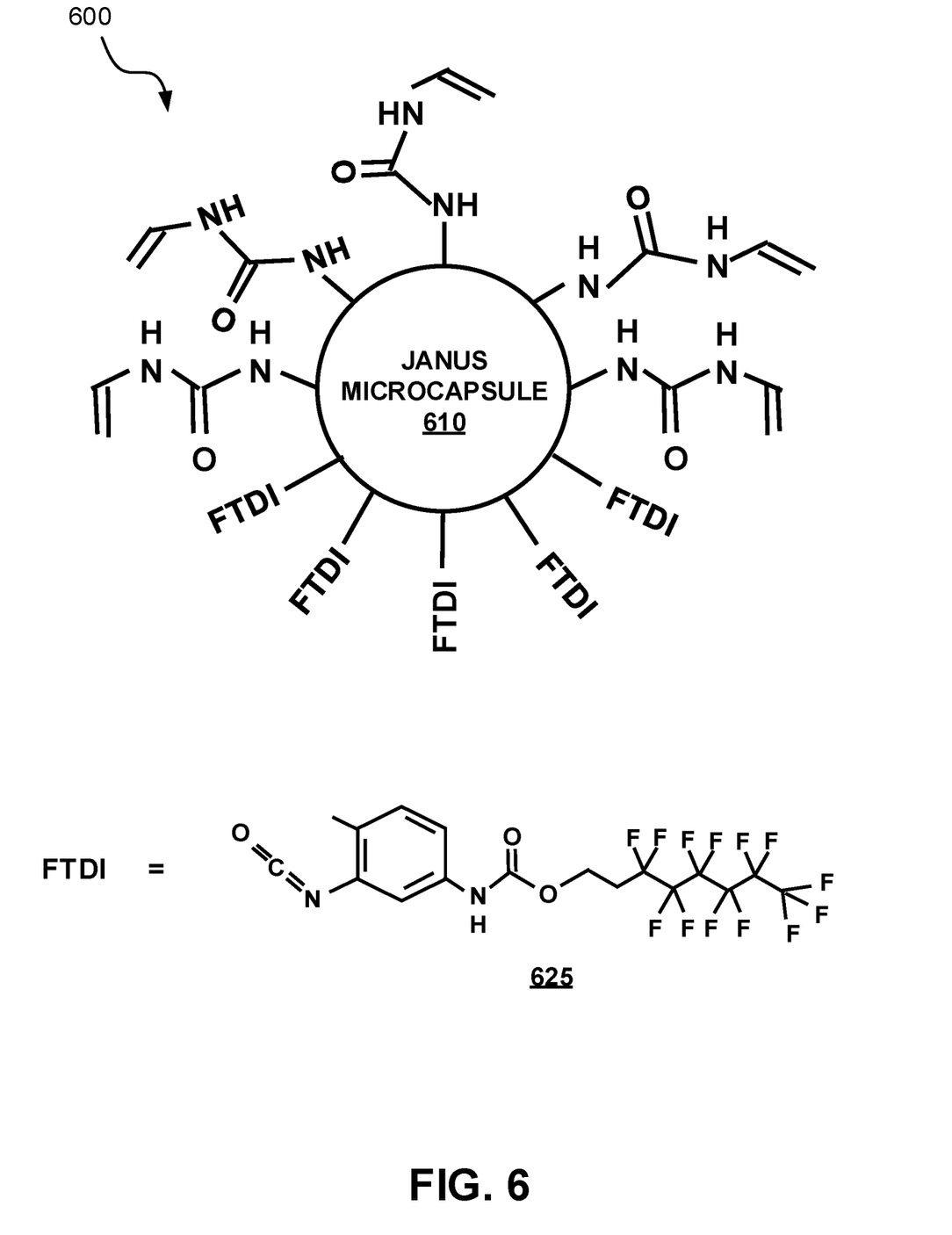
FIG. 6 depicts a diagrammatic representation of an example Janus microcapsule, according to various embodiments.

In various embodiments, process 100 continues with operation 150 to functionalize a second exposed surface of the functionalized one or more microcapsules. In some embodiments, the second exposed surface may be the surface previously embedded in the wax core. Functionalizing the second exposed surface of the one or more microcapsules may include introducing a second functionality to the microcapsules. In various embodiments, introducing the second functionality includes reacting a molecule containing the second functionality with the functionalized one or more microcapsules. A second functional group, different from the first functional group, may be reacted with the exposed surface of the microcapsule. In an example embodiment, the second functionality may be a lubricating or driving functionality. A lubricating functionality may be a fluorinated compound, such as a fluorinated hydrocarbon bound through a toluene diisocyanate linkage (or fluorine toluene diisocyanate (FTDI)) or any other compound containing fluorine. Examples of compounds containing fluorine include: difluorine, hydrogen fluorine, fluoropolymers, nonmetal fluorides, metal fluorides, etc. The microcapsule may become a Janus microcapsule once the second exposed surface of the microcapsule is functionalized, thus resulting in the microcapsule having at least two different functionalities. In an embodiment, the resulting Janus microcapsule may be Janus microcapsule 610 (FIG. 6).

In some embodiments, as discussed herein, the provided one or more microcapsules are already functionalized (e.g., the shell of the microcapsule includes a functional group), or pre-functionalized, before the functionalizing of the first exposed surface (operation 130). In these embodiments, functionalizing the second exposed surface of the one or more microcapsules may include adding a functional group to, or reacting a functional group with, the exposed surface of the microcapsule, where the exposed surface of the microcapsule includes an existing functional group.

In various embodiments, process 100 further includes adding an activator such as a catalyst and/or an initiator. In some embodiments, the activator is outside of the Janus microcapsule (e.g., the functionalized one or more microcapsules). Some self-healing payloads may react with an activator to enable their self-healing capabilities. In various embodiments, once the Janus microcapsule ruptures, the self-healing payload reacts with the activator. The activator may be chosen by those skilled in the art.

In various embodiments, process 100 further includes blending the functionalized one or more microcapsules into polymeric matrices. The polymeric matrices may have a functionality capable of reacting with the functionalized one or more microcapsules. The polymeric matrices functionality may be capable of reacting with either the first functionality or the second functionality of the microcapsules. The Janus microcapsules, when blended into the polymeric matrices, may then react with a polymer and form a bond that locks the Janus microcapsules in place within the polymer. Examples of polymers that can react with the Janus microcapsules can include epoxies, polyhydroxyurethanes, polycarbonates, polyesters, polyacrylates, polyimides, polyamides, polyureas, poly(vinyl-esters), etc. In some embodiments, the Janus microcapsules are blended into polymeric matrices by weight percent. If additional rheological control is needed, common materials may be used. Rheology may include deformation and flow of the polymers. In an example, when the Janus microcapsule includes a lubricating functionality, the resulting microcapsules after bonding with the polymers may have an abundant amount of fluorine groups. The abundance of fluorine groups may drive the capsules to the surface of the matrix polymer, then the microcapsules may cure and create a lubricious and healable material in case of abrasion.

In various embodiments, the process described herein may be used to functionalize additional surfaces of the one or more microcapsules. For example, two-thirds of the microcapsule may be embedded in the wax particle, and one-third of the microcapsule may become functionalized with a first functional group. Once the portion of the microcapsule is functionalized, the functionalized microcapsule may be partially removed from the wax core (e.g., one-third of the microcapsule embedded in the wax core, one-third of the microcapsule newly exposed, and one-third of the microcapsule functionalized). The newly exposed portion of the microcapsule may then be functionalized with a second functional group different from the first functional group. Once the second portion of the microcapsule is functionalized, the microcapsule may be completely removed from the wax core, thus exposing a third surface of the microcapsule. The third surface of the microcapsule may then be functionalized with a third functional group, resulting in a Janus microcapsule with three functionalities. A similar process may be used for any number of functionalities.

Figure 2:
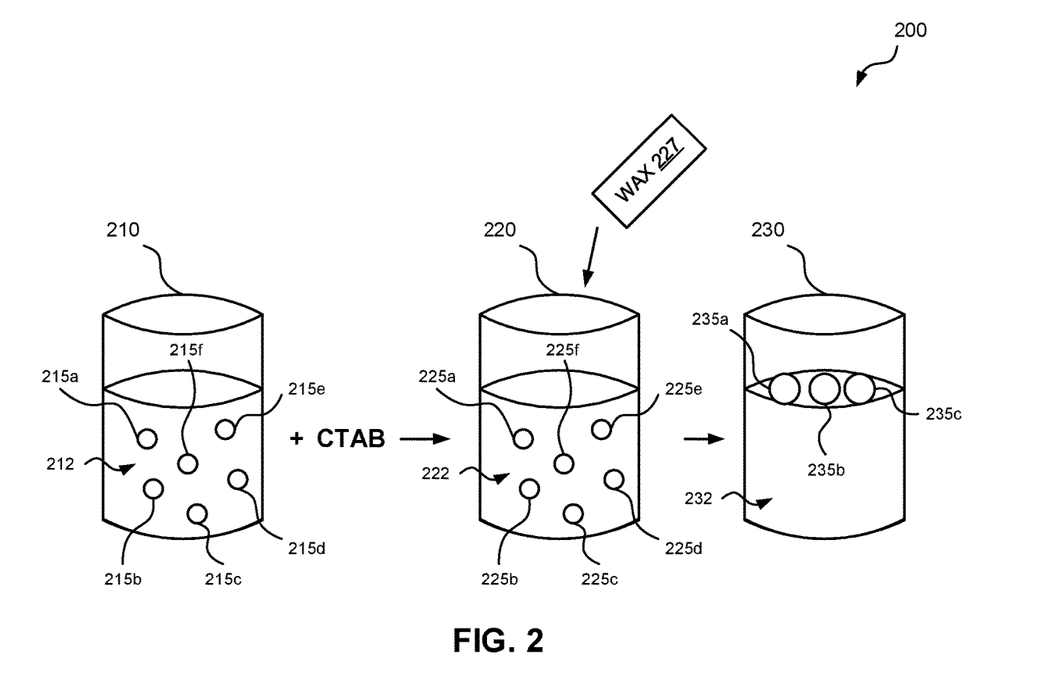
FIG. 2 depicts a schematic diagram of the formation of wax particles, according to various embodiments.
Figure 3:
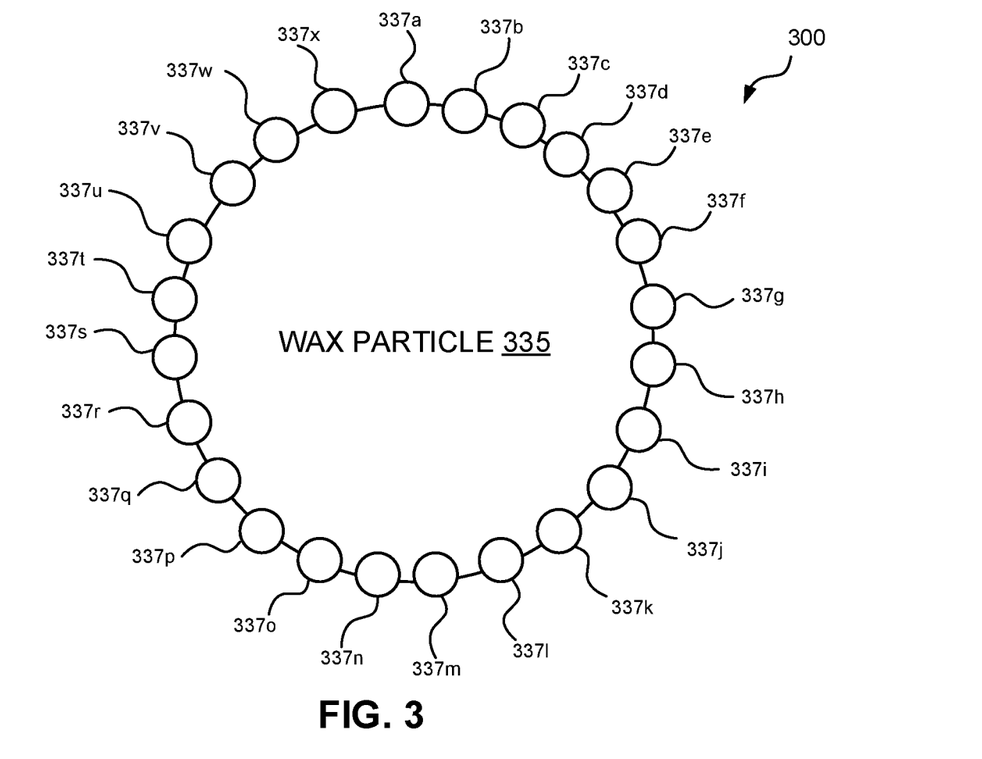
FIG. 3 depicts a schematic diagram of a wax particle, according to various embodiments.

Referring to FIG. 2, a schematic diagram illustrating a sample process 200 of forming wax particles 235a-235c is depicted, according to various embodiments. Process 200 is one possible reaction for forming wax particles 235a-235c, and is provided for illustrative purposes. FIG. 2 is a schematic diagram and is not drawn to scale. Additionally, the schematic diagram depicts a limited number of microcapsules and wax particles for illustrative purposes. Process 200 may include any number of microcapsules and any number of wax particles.

In various embodiments, forming a wax particle 235a-235c may include forming an aqueous mixture 210 containing the one or more microcapsules 215a-215f. In some embodiments, forming the aqueous mixture 210 includes dispersing microcapsules 215a-215f in an aqueous solution 212 (e.g., ethanol/water solution) and then mixing. The microcapsules 215a-215f may be dispersed into the aqueous solution 212 at an elevated temperature, in some embodiments, which allows for wax to melt when added to the mixture 210 (discussed herein). The aqueous mixture 210 may be a suspension, where the microcapsules 215a-215f are suspended through the aqueous solution 212, as depicted in FIG. 2.

In various embodiments, forming wax particles 235a-235c further includes partially hydrophobizing a surface of the one or more microcapsules 215a-215f. Hydrophobizing the surface of the microcapsules 215a-215f refers to increasing the hydrophobicity of the surface (e.g., the extent to which it repels or does not mix with water). Partially hydrophobizing the surface of the microcapsules 215a-215f may include making one portion of the surface (e.g., one half) hydrophobic. In some embodiments, cetyltrimethylammonium bromide (CTAB) is added to the aqueous mixture 210 to partially hydrophobize the surface of the microcapsules 215a-215f. A low concentration of CTAB may be used, to avoid a formation of a bilayer, or a film, at the surface of the microcapsule 215a-215f. Other surfactants may be used in place of CTAB. Example surfactants may include: cetylpyridinium chloride, benzalkonium chloride, benzethonium chloride, dimethyldioctadecylammonium chloride, dioctadecyldimethylammonium bromide, etc. Aqueous mixture 220 includes partially hydrophobized microcapsules 225a-225f and aqueous solution 222.

In various embodiments, forming the wax particles 235a-235c further includes adding wax 227 (e.g., paraffin wax, fluorinated wax, etc.) to the aqueous mixture 220. The wax 227 may be added at an elevated temperature so that the wax 227 is in liquid form. In some embodiments, the wax 227 may have a low melting temperature, so that the wax will melt below the degradation temperature of the microcapsule shell and below the boiling point of the payload. In various embodiments, the wax 227 is added, or deposited, on top of the microcapsule suspension in aqueous mixture 220. The solution 220, including the wax 227, may then be vigorously stirred at an elevated temperature. The elevated temperature may be a temperature above the melting temperature of the wax but below the boiling point of the payload. Stirring the solution at the elevated temperature may result in an adsorption at the aqueous solution (e.g., oil/water) interface, and may cause the hydrophobic portion, or side, of the microcapsule shell (of microcapsules 225a-225f) to adhere to the wax 227. Aqueous mixture 230 includes wax particles 235a-235c and aqueous solution 232. FIG. 3 depicts an example wax particle 335.

In various embodiments, forming the wax particles 235a-235c further includes cooling the aqueous mixture 230 to solidify the wax particles 235a-235c. After cooling (e.g., to room temperature), the wax 227 dissolved in the aqueous mixture 220 solidifies into solid droplets with the microcapsules 225a-225f partially extruding from the surface. These wax droplets with the partially exposed microcapsules 225a-225f are referred to herein as wax particles 235a-235c. FIG.

2 depicts wax particles 235a-235c at a surface of the aqueous solution 232. In various embodiments, wax particles 235a-235c may be substantially the same as wax particle 335 (FIG. 3).

In some embodiments, after the wax particles 235a-235c are formed, the wax particles 235a-235c are washed with an acid to remove the CTAB (or another surfactant) and expose the microcapsule surface.

Referring to FIG. 3, a schematic diagram 300 of a wax particle 335 is depicted, according to various embodiments. In some embodiments, wax particle 335 may be formed after an adsorption reaction, such as the reaction depicted in FIG. 2. Wax particle 335 may include microcapsules 337a-337x partially embedded in the wax surface. There may be one or more microcapsules embedded in the wax. In various embodiments, wax particle 335 is a colloidosome, with a wax core and microcapsules 337a-337x as colloid particles that make up the shell of the wax particle 335.

Referring to FIG. 4, a schematic diagram 400 of a microcapsule is depicted, according to various embodiments. Microcapsule 400 includes a polymeric shell 410 and a core 420. In some embodiments, the polymeric shell 410 may include an emulsifying agent and a cross-linking agent. In various embodiments, the polymeric shell may be flame-retardant. The core 420 may include a payload agent, with the payload agent enclosed within the microcapsule. In various embodiments, the payload agent may act as an emulsifying agent (e.g., emulsifier). The payload agent may be a self-healing agent, in some embodiments. In various embodiments, the payload agent is a polymerizable molecule such as cyclic olefins, norbornene, substituted norbornene, cyclooctadiene, substituted cyclooctadiene, lactones, arcrylates, acrylic acids, styrenes, isoprene, butadiene, and/or epoxies.

Referring to FIG. 5, a chemical reaction diagram illustrating a sample process 500 of functionalizing a surface of a microcapsule is depicted, according to various embodiments. Process 500 is only one possible reaction for functionalizing a surface of the microcapsule, and is illustrated for example purposes.

Process 500 may begin with a microcapsule 510 partially embedded in wax 515. In various embodiments, microcapsule 510 and wax 515 are part of a wax particle, such as wax particle 335. Microcapsule 510 may have pre-existing functionalities, or functional groups. In process 500, microcapsule 510 has a pre-existing amine functionality. Although the amines are depicted as bound to the surface of the microcapsule, the amines may be free near the surface of the microcapsule as part of the shell.

Process 500 may continue by reacting a functional group with the exposed surface of the microcapsule. In process 500, vinyl isocyanate 520 is reacted with the exposed surface and the amine on the exposed surface of the microcapsule. The vinyl isocyanate 520 may have a matrix bonding functionality, in some embodiments. Once the vinyl isocyanate 520 is reacted with the microcapsule 510, the microcapsule is functionalized, resulting in microcapsule 530 with a functionalized exposed surface. In various embodiments, the microcapsule 530 surface, or shell, that is embedded in the wax may not be functionalized by the vinyl isocyanate 520.

In various embodiments, a similar process is used to functionalize a second surface of the microcapsule 530, once the wax 535 is removed, or separated, from the microcapsule 530.

Referring to FIG. 6, a diagrammatic representation 600 of an example Janus microcapsule 610 is depicted, according to various embodiments. In various embodiments, Janus microcapsule 610 is formed using process 100 (FIG. 1). In an embodiment, a second surface (the surface previously embedded in the wax) of microcapsule 530 (FIG. 5) may be functionalized to form Janus microcapsule 610.

In various embodiments, Janus microcapsule 610 has one surface of the microcapsule having been functionalized by vinyl isocyanate 520, as depicted in FIG. 5. Vinyl isocyanate 520 may have a matrix bonding functionality, in some embodiments. The second surface of the Janus microcapsule 610 may have a fluorine toluene diisocyanate (FTDI) functionality. In some embodiments, FTDI 625 may have a lubricating functionality. The surface of the Janus microcapsule 610 may be functionalized by reacting FTDI 625 with the exposed surface, or the previously embedded surface, of the microcapsule. The exposed surface of the Janus microcapsule 610 may functionalized by reacting the exposed surface with FTDI 625 in toluene. In some embodiments, the functionalities may overlap on the shell of the Janus microcapsule 610, but the functionalities may be different enough so there is a small, sometimes miniscule, amount of overlap.

In various embodiments, a Janus microcapsule with two or more functionalities on the surface, such as Janus microcapsule 610, is included in an article of manufacture. In some embodiments, the article of manufacture includes a material that contains the Janus microcapsule. The material can be a resin, plastic, adhesive, or polymer. Examples of polymer materials can include polyurethane, epoxies, polyhydroxyurethane, polycarbonates, polyester, polyacrylates, polyimides, polyamides, polyureas, poly(vinyl-ester), etc. The article of manufacture may further include an electronic component.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are not to be construed as limiting. One skilled in the art would recognize that a variety of synthetic reactions may be used that vary in reaction conditions, components, methods, etc., which ultimately generate one or both of flame retardant itaconic acid-based compounds and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of forming a microcapsule, wherein the microcapsule has a plurality of functionalities on a surface, the method comprising:
   providing one or more microcapsules;
   forming one or more wax particles, each of the one or more wax particles including a wax core, the wax core having the one or more microcapsules partially embedded therein;
   functionalizing a first exposed surface of the one or more microcapsules to generate one or more functionalized microcapsules;
   removing the one or more functionalized microcapsules from the wax core; and
   functionalizing a second exposed surface of the one or more functionalized microcapsules, the second exposed surface previously embedded in the wax core.

2. The method of claim 1, wherein forming the one or more wax particles comprises:
   forming an aqueous mixture, the aqueous mixture including the one or more microcapsules;
   partially hydrophobizing a surface of the one or more microcapsules in the aqueous mixture;
   adding wax to the aqueous mixture at an elevated temperature; and
   cooling the aqueous mixture to solidify the wax particles.

3. The method of claim 1, wherein functionalizing the first exposed surface of the one or more microcapsules includes introducing a first functionality to the first exposed surface; and wherein functionalizing the second exposed surface of the one or more microcapsules includes introducing a second functionality to the second exposed surface.

4. The method of claim 3, wherein introducing the first functionality includes reacting a molecule providing the first functionality with the first exposed surface.

5. The method of claim 3, wherein introducing the second functionality includes reacting a molecule containing the second functionality with the second exposed surface.

6. The method of claim 3, wherein the first functionality is a matrix bonding functionality.

7. The method of claim 6, wherein the matrix bonding functionality includes at least one of vinyls, amines, epoxies, allyls, and acrylates.

8. The method of claim 3, wherein the second functionality is a lubricating functionality.

9. The method of claim 8, wherein the lubricating functionality includes a fluorine-containing molecule.

10. The method of claim 1, wherein the one or more functionalized microcapsules is removed from the wax core using a hydrocarbon solvent.

11. The method of claim 1, further comprising:
   blending the one or more functionalized microcapsules into polymeric matrices, the polymeric matrices having a functionality capable of reacting with the one or more functionalized microcapsules.

12. The method of claim 1, wherein the microcapsule includes a self-healing payload.

* * * * *